(12) United States Patent
Lin

(10) Patent No.: US 7,276,625 B2
(45) Date of Patent: Oct. 2, 2007

(54) PROCESS FOR PRODUCTION OF A CARBOXYLIC ACID/DIOL MIXTURE SUITABLE FOR USE IN POLYESTER PRODUCTION

(75) Inventor: Robert Lin, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/271,058

(22) Filed: Oct. 15, 2002

(65) Prior Publication Data

US 2004/0073059 A1   Apr. 15, 2004

(51) Int. Cl.
*C07C 51/16* (2006.01)
*C07C 51/42* (2006.01)
*C07C 69/52* (2006.01)

(52) U.S. Cl. ............... 562/485; 560/224; 562/487; 562/412; 562/416

(58) Field of Classification Search ............ 560/76, 560/224; 562/412, 487, 485, 416
See application file for complete search history.

(56) References Cited

U.S. PATENT DOCUMENTS

| | | | |
|---|---|---|---|
| 3,057,909 A | 10/1962 | Sebelist et al. | |
| 3,064,044 A | 11/1962 | Baldwin | |
| 3,584,039 A | 6/1971 | Meyer | |
| 3,683,018 A | 8/1972 | Longland, Jr. | |
| 3,839,436 A | 10/1974 | Longland, Jr. | |
| 3,850,983 A | 11/1974 | Park | |
| 3,931,305 A | 1/1976 | Fisher | |
| 4,051,178 A | 9/1977 | Kimura et al. | |
| 4,158,738 A * | 6/1979 | Scott et al. | 562/416 |
| 4,201,871 A | 5/1980 | Tanouchi et al. | |
| 4,212,995 A | 7/1980 | Shiraki | |
| 4,268,690 A | 5/1981 | Komatsu et al. | |
| 4,330,676 A | 5/1982 | Moxham | |
| 4,334,086 A | 6/1982 | Hanotier et al. | |
| 4,357,475 A | 11/1982 | Hanotier et al. | |
| 4,380,662 A | 4/1983 | Hanotier et al. | |
| 4,500,732 A | 2/1985 | Petty-Weeks et al. | |
| 4,588,414 A | 5/1986 | Takegami et al. | |
| 4,707,274 A | 11/1987 | Donhauser et al. | |
| 4,782,181 A | 11/1988 | James | |
| 4,812,233 A | 3/1989 | Coenen et al. | |

(Continued)

FOREIGN PATENT DOCUMENTS

CA   1067095   11/1979

(Continued)

OTHER PUBLICATIONS

U.S. Appl. No. 10/383,126, filed Mar. 6, 2003, Lin.

(Continued)

*Primary Examiner*—Taylor Victor Oh
(74) *Attorney, Agent, or Firm*—Steven A. Owen; Bernard J. Graves, Jr.

(57) ABSTRACT

In this invention, a process is provided by which a carboxylic acid/diol mixture suitable as starting material for a polyester production is obtained from a decolorized carboxylic acid solution without isolation of a substantially dry carboxylic acid solid. More specifically, in this invention, a process is provided by which a terephthalic acid/ethylene glycol mixture suitable as starting material for a polyester production is obtained from a decolorized terephthalic acid solution without isolation of a substantially dry terephthalic acid solid.

25 Claims, 2 Drawing Sheets

U.S. PATENT DOCUMENTS

| | | | |
|---|---|---|---|
| 4,861,919 A | 8/1989 | Robbins et al. | |
| 4,892,972 A * | 1/1990 | Schroeder et al. | 562/487 |
| 4,939,297 A | 7/1990 | Browder et al. | |
| 5,008,450 A | 4/1991 | Yamamoto et al. | |
| 5,080,721 A | 1/1992 | Flanigan et al. | |
| 5,095,146 A | 3/1992 | Zeitlin et al. | |
| 5,107,874 A | 4/1992 | Flanigan et al. | |
| 5,116,423 A | 5/1992 | Kokkonen et al. | |
| 5,143,554 A | 9/1992 | Koyama et al. | |
| 5,175,355 A * | 12/1992 | Streich et al. | 562/485 |
| 5,200,557 A | 4/1993 | Gee et al. | |
| 5,454,959 A | 10/1995 | Stevens | |
| 5,476,919 A * | 12/1995 | Schaeffer | 528/272 |
| 5,527,957 A | 6/1996 | Hindmarsh et al. | |
| 5,563,293 A | 10/1996 | Hindmarsh et al. | |
| 5,567,842 A | 10/1996 | Izumisawa et al. | |
| 5,583,254 A | 12/1996 | Turner et al. | |
| 5,616,792 A | 4/1997 | Bartos et al. | |
| 5,635,074 A | 6/1997 | Stenstrom et al. | |
| 5,643,468 A | 7/1997 | Ure | |
| 5,653,673 A | 8/1997 | Desai et al. | |
| 5,676,847 A | 10/1997 | Yamamoto et al. | |
| 5,679,846 A | 10/1997 | Hindmarsh et al. | |
| 5,684,187 A | 11/1997 | Ohkoshi et al. | |
| 5,698,734 A | 12/1997 | Turner et al. | |
| 5,712,412 A | 1/1998 | Inary et al. | |
| 5,777,161 A | 7/1998 | Inary | |
| 5,840,965 A | 11/1998 | Turner et al. | |
| 5,840,968 A | 11/1998 | Lee et al. | |
| 5,925,786 A | 7/1999 | Isayama et al. | |
| 5,955,394 A | 9/1999 | Kelly | |
| 5,971,907 A | 10/1999 | Johannemann et al. | |
| 5,973,196 A | 10/1999 | Takano et al. | |
| 6,013,835 A | 1/2000 | Lee et al. | |
| 6,153,790 A | 11/2000 | June et al. | |
| 6,162,837 A | 12/2000 | Gerking et al. | |
| 6,228,215 B1 | 5/2001 | Hoffman, Jr. | |
| 6,297,348 B1 | 10/2001 | Rodden et al. | |
| 6,307,099 B1 | 10/2001 | Turner et al. | |
| 6,495,044 B1 | 12/2002 | Verdoes | |
| 6,517,733 B1 | 2/2003 | Carlson | |
| 6,797,073 B1 | 9/2004 | Teruggi et al. | |
| 2003/0004372 A1 | 1/2003 | Piras et al. | |
| 2004/0176635 A1* | 9/2004 | Lin et al. | 560/80 |
| 2004/0245176 A1 | 12/2004 | Parker et al. | |
| 2005/0087215 A1 | 4/2005 | Miyahara et al. | |

FOREIGN PATENT DOCUMENTS

| | | | |
|---|---|---|---|
| CN | 1299806 A | 6/2001 | |
| DE | 31 28 474 A1 | 6/1982 | |
| DE | 33 28 543 A1 | 3/1985 | |
| EP | 0111784 B1 | 2/1986 | |
| EP | 0 370 083 B1 | 6/1994 | |
| GB | 994 769 | 6/1965 | |
| GB | 1059840 | 2/1967 | |
| GB | 1 334 452 | 10/1973 | |
| GB | 1 498 031 | 1/1978 | |
| GB | 1 589 310 | 5/1981 | |
| JP | 48-15848 A | 2/1973 | |
| JP | 48026740 | * | 4/1973 |
| JP | 48-67239 A | 9/1973 | |
| JP | 52-113940 A | 11/1977 | |
| JP | 53-53634 A | 5/1978 | |
| JP | 53-90233 A | 8/1978 | |
| JP | 53-90234 A | 8/1978 | |
| JP | 55-33421 A | 3/1980 | |
| JP | 7-149690 A | 6/1995 | |
| JP | 7-291896 A | 11/1995 | |
| JP | 9-255619 A | 9/1997 | |
| JP | 9-286758 A | 11/1997 | |
| JP | 9-286759 A | 11/1997 | |
| JP | 10-36313 A | 2/1998 | |
| JP | 2003-62405 A | 3/2003 | |
| JP | 2003-128624 A | 5/2003 | |
| SU | 1042809 A | 9/1983 | |
| WO | WO 93/24440 A1 | 12/1993 | |
| WO | WO 98/38150 A1 | 9/1998 | |
| WO | WO 99/08990 A1 | 2/1999 | |
| WO | WO 99/31038 A1 | 6/1999 | |
| WO | WO 03/020680 A1 | 3/2003 | |

OTHER PUBLICATIONS

Arun Pal Aneja and Viney Pal Aneja, "The Effect of Water and Air Contamination on Poly (Ethylene) Terephthalate) Formation", *Polymer Engineering Reviews*, 1982, pp. 123-133, vol. 2, No. 2.

M. Maties, R. Bacai Oglu, R.F. Paie & H.H. Glatt, "Study of Di- and Polyesterification, I. Esterification of Ethylene and Diethylene Glycols with Acetic Acid", (1978), Chemical Bulletin of the Technical University of Timisoara, 23(37), pp. 73-76.

U.S. Appl. No. 10/271,058, filed Oct. 15, 2002, Lin et al.

Allen, Norman S., Edge, Michelle, Daniels, James, Royall, David, "*Spectroscopic Analysis of Organic Contaminants in Terphthalic Acid: Colour Implications in Poly(ethylene terephthalate) Manufacture*", Polymer Degradation and Stability, 1998, pp. 373-383, 62, Great Britain.

Copending U.S. Appl. No. 10/768,678, filed Jan. 15, 2004.

PCT International Search Report.

USPTO Office Action dated Mar. 3, 2006 for U.S. Appl. No. 10/383,126.

USPTO Office Action dated May 30, 2006 for U.S. Appl. No. 11/077,481.

USPTO office action dated Aug. 4, 2006 for copending U.S. Appl. No. 10/758,678.

USPTO Office Action dated Sep. 14, 2005 for copending U.S. Appl. No. 11/077,481.

USPTO Notice of Allowability dated Jan. 8, 2007 for copending U.S. Appl. No. 10/758,678.

USPTO Office Action dated May 7, 2007 for copending U.S. Appl. No. 11/076,840.

* cited by examiner

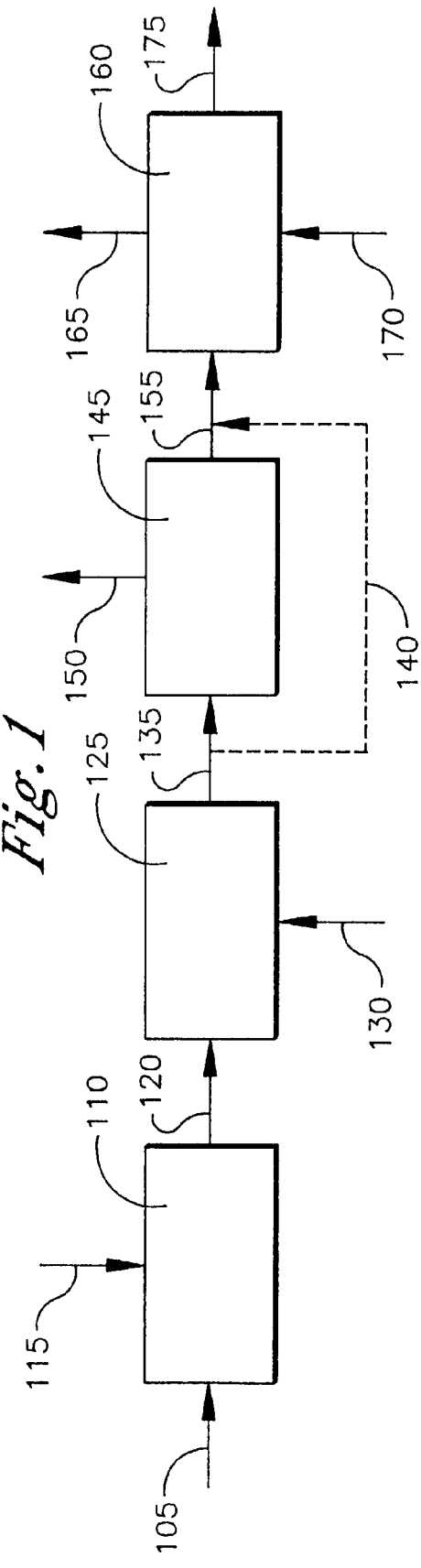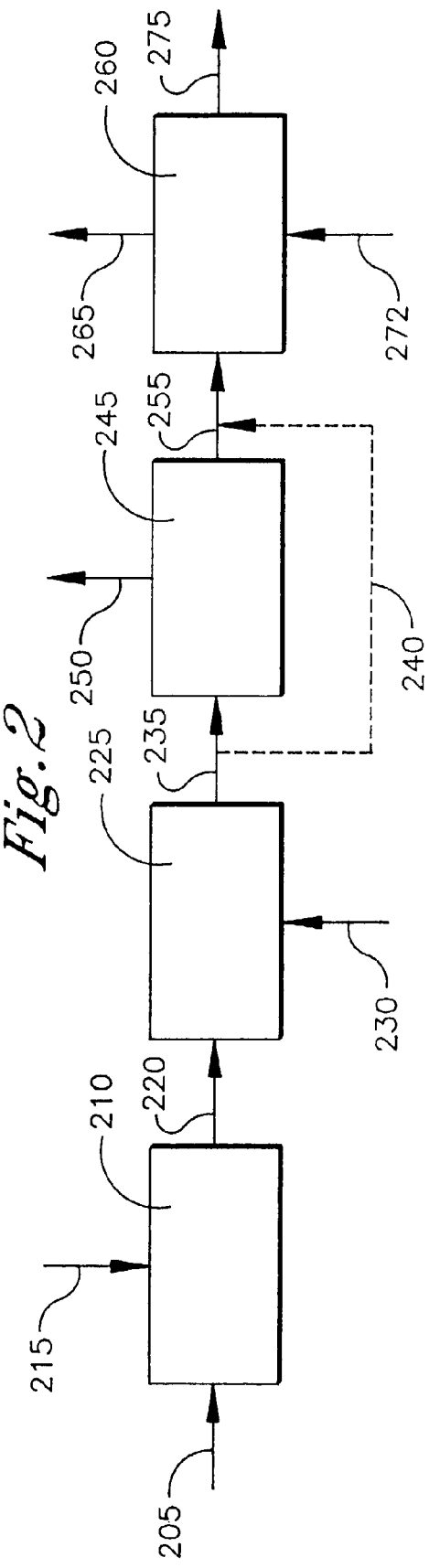

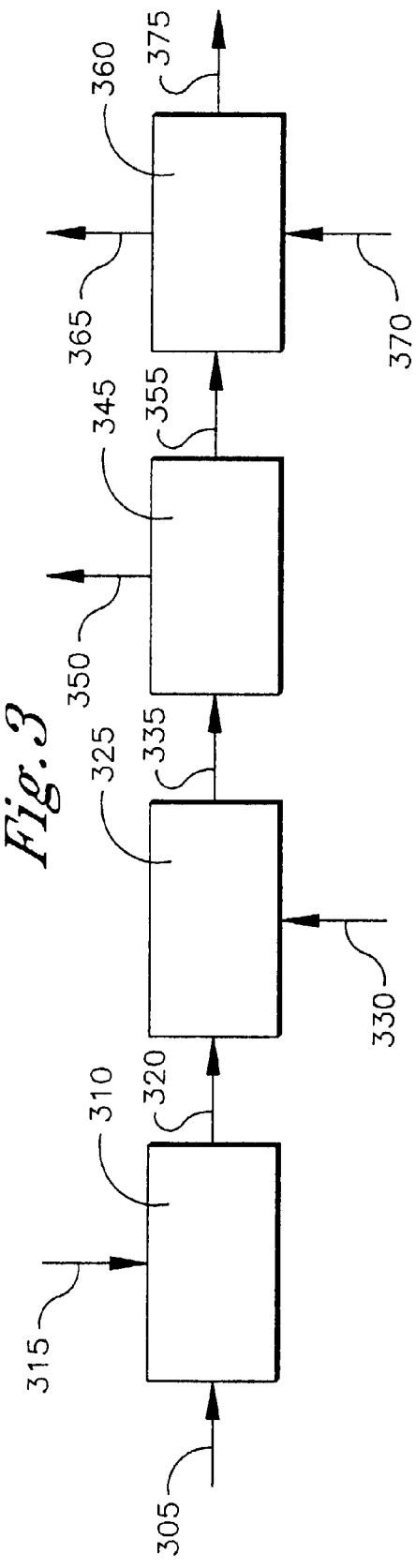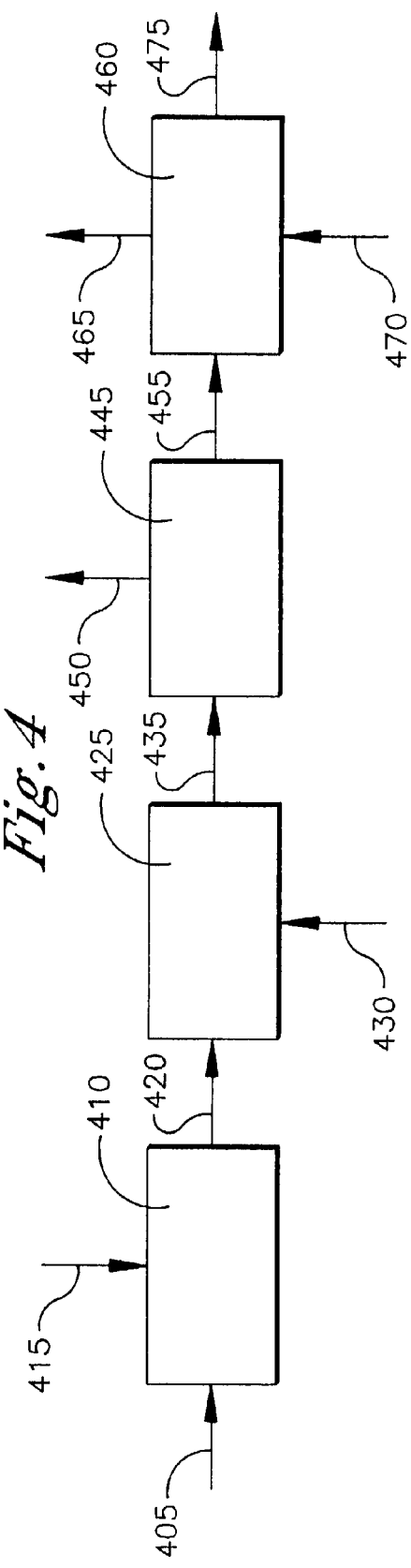

PROCESS FOR PRODUCTION OF A CARBOXYLIC ACID/DIOL MIXTURE SUITABLE FOR USE IN POLYESTER PRODUCTION

FIELD OF INVENTION

The present invention relates to a process by which a carboxylic acid/diol mixture is obtained from a decolorized carboxylic acid solution without isolation of a substantially dry carboxylic acid solid. More specifically, the present invention relates to a process by which a terephthalic acid/ethylene glycol mixture suitable as a starting material for polyester production is obtained from a decolorized terephthalic acid solution without isolation of a substantially dry terephthalic acid solid.

BACKGROUND OF THE INVENTION

Thermoplastic polyesters are step growth polymers that are useful when made to high molecular weights. The first step in a common method of producing a polyester such as polyethylene terephthalate (PET) is an esterification or ester-exchange stage where a diacid (typically terephthalic acid) reacts with an appropriate diol (typically ethylene glycol) to give a bis(hydroxyalkyl)ester and some linear oligomers. Water is evolved at this stage and is usually removed by fractional distillation.

Pursuant to the goal of making polyethylene terephthalate and other polyesters, a great deal of patent literature is dedicated to the describing processes for preparing terephthalic acid/ethylene glycol mixtures suitable as starting material. In general, these inventions describe specific mixing schemes with a purified terephthalic acid solid and liquid ethylene glycol as starting materials. Additionally, there is a substantial body of literature devoted to producing a purified terephthalic acid in the powder form that is suitable for use in producing PET. The objective of this invention is to describe a process by which a terephthalic acid/ethylene glycol mixture suitable as starting material for polyester production is obtained from a decolorized terephthalic acid solution without isolation of a substantially dry terephthalic acid solid.

A number of processes for producing the purified terephthalic acid solid have been developed and are commercially available. Usually, the purified terephthalic acid solid is produced in a multi-step process wherein a crude terephthalic acid is produced. The crude terephthalic acid does not have sufficient quality for direct use as starting material in commercial PET. Instead, the crude terephthalic acid is usually refined to purified terephthalic acid solid.

Liquid phase oxidation of p-xylene produces crude terephthalic acid. The crude terephthalic acid is dissolved in water and hydrogenated for the purpose of converting 4-carboxybenzaldehyde to p-toluic acid, which is a more water-soluble derivative, and for the purpose of converting characteristically yellow compounds to colorless derivatives. Any 4-carboxybenzaldehyde and p-toluic acid in the final purified terephthalic acid product is particularly detrimental to polymerization processes as they act as a chain terminator during the condensation reaction between terephthalic acid and ethylene glycol in the production of PET. Typical purified terephthalic acid contains on a weight basis less than 25 parts per million (ppm) 4-carboxybenzaldehyde and less than 150 ppm p-toluic acid.

The crude terephthalic acid typically contains on a weight basis from about 800 to 7,000 parts per million (ppm) 4-carboxybenzaldehyde and about 200 to 1,500 ppm p-toluic acid as the main impurities. The crude terephthalic acid also contains lesser amounts, about 20-200 ppm range, of yellow color aromatic compounds having the structures of benzil, fluorenone, and/or anthraquinone, which are characteristically yellow compounds as impurities resulting from coupling side reactions occurring during oxidation of p-xylene. It is necessary to purify the crude terephthalic acid when using it as a starting material for producing polyester fiber, which requires a purified terephthalic acid as a starting material.

Such a purification process typically comprises adding water to the crude terephthalic acid to form a crude terephthalic acid solution, which is heated to dissolve the crude terephthalic acid. The crude terephthalic acid solution is then passed to a reactor zone in which the solution is contacted with hydrogen in the presence of a heterogeneous catalyst at temperatures of about 200° to about 375° C. This reduction step converts the various color bodies present in the crude terephthalic acid to colorless products. The principal impurity, 4-carboxybenzaldehyde, is converted to p-toluic acid.

Typical crude terephthalic acid contains excessive amounts of both 4-carboxybenzaldehyde and p-toluic acid on a weight basis. Therefore, to achieve less than 25 ppmw 4-carboxybenzaldehyde and less than 150 ppmw p-toluic acid in the purified terephthalic acid requires mechanisms for purifying the crude terephthalic acid and removing the contaminants.

Subsequent separation and isolation of the purified terephthalic acid can be accomplished via a wide variety of separation methods including crystallization, centrifugation, filtration, extraction and combinations thereof followed by drying. These processes are described in U.S. Pat. Nos. 4,500,732; 5,175,355; and 5,583,254; all of which are herein incorporated by reference. It is necessary to perform a separation step due the nature of the crude terephthalic acid feedstock to the hydrogenation process.

A number of processes have been developed for producing a purified terephthalic acid solid from crude terephthalic acid. In general, the common features among these processes are as follows:

Step (1) is decolorization of the crude terephthalic acid usually via hydrogenation treatment in an aqueous medium;

Step (2) is purification/separation of the terephthalic acid from partial oxidation products usually via fractional crystallization followed by liquor exchange with contaminant-free water; and Step (3) is production of a solid purified terephthalic acid product with consistent material handling properties usually via crystallization of terephthalic acid followed by drying of purified terephthalic acid from water.

The resultant purified terephthalic acid powder along with ethylene glycol are starting materials in the production of polyesters specifically PET. Because the difficulty in handling, mixing, and dissolving terephthalic acid solids, the purified terephthalic acid solid is usually mixed with ethylene glycol to form a paste prior to introduction into an esterification reactor system.

In the present invention, a novel process has been discovered resulting in fewer steps than the currently employed processes. The primary utility of the invention is reduction of capital and operating costs associated with the isolation of a terephthalic acid powder. In the conventional approach toward producing terephthalic acid, the post-hydrogenated aqueous solution is passed to a series of crystallizer vessels for the purpose of purifying the terephthalic acid by crystallization and for the purpose of obtaining a uniform particle size distribution necessary for good flowability of purified terephthalic powder. Further, the p-toluic acid contaminated mother liquor from the crystallization process must be removed prior to a drying step to isolate the purified terephthalic powder.

In on embodiment of the present invention, the crude terephthalic acid solution with low concentrations of p-toluic acid and 4-carboxybenzaldehyde is hydrogenated to form a decolorized terephthalic acid solution. Starting with crude terephthalic acid with low concentrations of the p-toluic acid and 4-carboxybenzaldehyde eliminates the need for separation of p-toluic acid-contaminated mother liquor from the terephthalic acid. Hence, the decolorized terephthalic acid solution can be directly combined with ethylene glycol in an esterification zone to produce a terephthalic acid/ethylene glycol mixture. By bypassing conventional processes for producing a purified terephthalic acid powder, the need for the equipment necessary to purify and isolate purified terephthalic powder is eliminated.

Another surprising and seemingly contradictory aspect of the invention is the benefits of addition of large amounts of water to the esterification reaction starting materials. This is directly contrary to accepted esterification procedures. The esterification reaction:

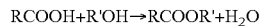

is generally not complete. The water formed in the course of the reaction tends to react with the ester to hydrolyze it, i.e. to regenerate the original alcohol and acid. In order to drive the reaction toward the ester, the prior art teaches removal of water from the system by a variety of methods such as distillation or dehydration with a hydrophilic compound. According to conventional esterification procedures, it is non-intuitive to add large amount of the water to the acid/alcohol starting material.

SUMMARY OF THE INVENTION

The present invention relates to a process by which a carboxylic acid/diol mixture is obtained from a decolorized carboxylic acid solution without isolation of a substantially dry carboxylic acid solid. More specifically, the present invention relates to a process for the production of a terephthalic acid/ethylene glycol mixture suitable as feedstock for the production of commercial PET. The resulting process has fewer steps than currently employed processes and can be operated at lower operating cost and constructed at lower capital cost. Specifically, the present invention incorporates a direct displacement of water with ethylene glycol step following hydrogenation treatment of crude terephthalic acid. Incorporation of the displacement step eliminates the need to isolate a purified terephthalic acid solid thereby eliminating the need for crystallization, solid-liquid separation, and solids handling equipment normally found in commercial purified terephthalic acid processes.

It is an object of this invention to provide a process for producing a carboxylic acid/diol mixture without isolation of a substantially dry carboxylic acid solid.

It is another object of this invention to provide a process for producing a terephthalic acid/diol mixture without isolation of a substantially dry terephthalic acid solid.

It is another object of this invention to provide a process for producing a terephthalic acid/ethylene glycol mixture without isolation of a substantially dry terephthalic acid solid.

It is another object of this invention to provide a process for producing a terephthalic acid/ethylene glycol mixture without isolation of a substantially dry terephthalic acid solid by vaporization of the water from a decolorized terephthalic acid solution with enthalpy supplied by ethylene glycol in a esterification reactor.

It is another object of this invention to provide a process for producing a terephthalic acid/ethylene glycol mixture without isolation of a substantially dry terephthalic acid solid by removing water from a decolorized terephthalic acid solution through the use of solid liquid displacement devices such as centrifuges, filters or cyclones.

In a first embodiment of this invention, a process for producing a carboxylic acid/diol mixture is provided, the process comprising adding a diol to a decolorized carboxylic acid solution in an esterification reactor zone to remove a portion of the water to form the carboxylic acid/diol mixture; wherein said carboxylic acid and diol subsequently reacts in the esterification zone to form a hydroxy alkyl ester stream. Typically, the carboxylic acid is selected from a group consisting of terephthalic acid, isophthalic acid, naphthalene dicarboxylic acid, and mixtures thereof In another embodiment of this invention, a process for producing a carboxylic acid/diol mixture is provided, the process comprising the following steps:

(a) mixing a crude carboxylic acid powder with water in a mixing zone to form a crude carboxylic acid solution; wherein the carboxylic acid is selected from a group consisting of terephthalic acid, isophthalic acid, naphthalene dicarboxylic acid, and mixtures thereof;

(b) decolorizing the crude carboxylic acid solution in a reactor zone to produce a decolorized carboxylic acid solution.

(c) optionally, flashing the decolorized carboxylic acid solution in a flashing zone to remove a portion of the contaminated water from the decolorized carboxylic acid solution; and (d) adding a diol to the decolorized carboxylic acid solution in an esterification reactor zone to vaporize a portion of the water to form the carboxylic acid/diol mixture; wherein the carboxylic acid and diol subsequently reacts in the esterification zone to form a hydroxy alkyl ester stream.

In another embodiment of this invention, a process for producing a terephthalic acid/diol mixture is provided, the process comprising vaporizing a decolorized terephthalic acid solution with a diol in an esterification reactor zone to remove a portion of the water to form the terephthalic acid/diol mixture; wherein the terephthalic acid and diol subsequently reacts in the esterification zone to form a hydroxyalky ester stream.

In another embodiment of this invention, a process for producing a terephthalic acid/diol mixture is provided, the process comprising the following steps:

(a) mixing a crude terephthalic acid powder with water in a mixing zone to form a crude terephthalic acid solution;

(b) decolorizing the crude terephthalic acid solution in a reactor zone to form a decolorized terephthalic acid solution;

(c) optionally, flashing the decolorized terephthalic acid solution in a flashing zone to remove a portion of water from the aqueous terephthalic solution; and (d) adding a diol to the decolorized terephthalic acid solution in an esterification reactor zone to remove a portion of water to form the terephthalic acid/diol mixture; wherein the terephthalic acid and diol subsequently reacts to from a hydroxy alkyl ester stream.

In another embodiment of this invention, a process for producing a carboxylic acid/diol mixture is provided, the process comprising removing a portion of the p-toluic contaminated water in an terephthalic acid aqueous slurry by adding a diol in a liquor removal zone to produce said carboxylic acid/ethylene glycol mixture.

In another embodiment of this invention, a process for producing a carboxylic acid/diol mixture is provided, the process comprising the following steps:

(a) mixing a crude carboxylic acid powder with water in a mixing zone to form a crude carboxylic acid solution;

(b) decolorizing the crude carboxylic acid in a reactor zone to produce a decolorized carboxylic acid solution.

(c) crystallizing the decolorized carboxylic acid solution in a crystallization zone to form a terephthalic acid aqueous slurry; and (d) removing a portion of the contaminated water in said terephthalic acid aqueous slurry by adding a diol in a liquor removal zone to produce said carboxylic acid/diol mixture.

In another embodiment of this invention, a process for producing a terephthalic acid/ethylene glycol mixture is provided, the process comprising removing a portion of the p-toluic contaminated water in an terephthalic acid aqueous slurry by adding a diol in a liquor removal zone to produce the terephthalic acid/diol mixture.

In another embodiment of this invention, a process for producing a terephthalic acid/ethylene glycol mixture is provided, the process comprising the following steps:

(a) mixing a crude terephthalic acid powder with water in a mixing zone to form a crude terephthalic acid solution;

(b) decolorizing the crude terephthalic acid solution in a reactor zone to form a decolorized terephthalic acid solution;

(c) crystallizing of the decolorized terephthalic acid solution in a crystallization zone to form an terephthalic acid aqueous slurry; and (d) removing a portion of p-toluic acid contaminated water in the terephthalic acid aqueous slurry by adding a diol in a liquor removal zone to produce the terephthalic acid/diol mixture.

These objects, and other objects, will become more apparent to others with ordinary skill in the art after reading this disclosure.

BRIEF DESCRIPTION OF THE DRAWINGS

FIG. 1 illustrates one embodiment of this invention. A process is provided utilizing carboxylic acid powder to produce a carboxylic acid/diol mixture with the carboxylic acid and diol subsequently reacting to form a hydroxy alkyl ester stream FIG. 2 illustrates an alternative embodiment of this invention. A process is provided utilizing a terephthalic acid powder to produce a terephthalic acid/diol mixture with the terephthalic acid and diol subsequently react to form a hydroxy alkyl ester stream FIG. 3 illustrates another alternative embodiment of this invention. A process is provided which utilizes a carboxylic acid powder to produce a carboxylic acid/diol mixture.

FIG. 4 illustrates yet another alternative embodiment of this invention. A process is provided where a crude terephthalic acid powder is utilized to produce a terephthalic acid/diol mixture.

DETAILED DESCRIPTION OF THE INVENTION

In the first embodiment of this invention a process for producing a carboxylic acid/diol mixture the process comprising the adding a diol to a decolorized carboxylic acid solution in an esterification reactor zone to remove a portion of the water to form the carboxylic acid/diol mixture; wherein the carboxylic acid is selected from a group consisting of terephthalic acid, isophthalic acid, naphthalene dicarboxylic acid, and mixtures thereof; wherein said carboxylic acid and diol subsequently reacts in the esterification zone to from a hydroxy alkyl ester stream.

The esterification reactor zone, the decolorized carboxylic acid solution and a process to produce the decolorized carboxylic acid solution is described subsequently in a second embodiment of this invention.

In the second embodiment of this invention a process for producing a carboxylic acid/diol mixture is provided as shown in FIG. #1.

Step (1) comprises mixing a crude carboxylic acid powder in conduit 105 with water in conduit 115 in a mixing zone 110 to form a crude carboxylic acid solution in conduit 120; Typically, the carboxylic acid is selected from a group consisting of terephthalic acid, isophthalic acid, naphthalene dicarboxylic acid, and mixtures thereof. The mixing of the crude carboxylic powder in conduit 105 with water in conduit 115 in the mixing zone 110 can be accomplished by any means known in the art. The mixing zone 110 can be any vessel or equipment capable of mixing the crude carboxylic acid powder. The temperature and pressure of the mixing zone 110 is that which is sufficient to properly slurry the crude carboxylic acid powder in conduit 105 with water in conduit 115. Typically, the crude carboxylic acid powder in conduit 105 is slurried with water in conduit 115 in mixing zone 110 at a concentration of 15-35% by weight.

Step (2) is decolorizing the crude carboxylic acid solution in conduit 120 in a reactor zone 125 to produce a decolorized carboxylic acid solution 135.

The decolorizing of the crude carboxylic acid solution in conduit 120 can be accomplished by any means known in the art. Preferably, the decolorizing can be accomplished by reacting the crude carboxylic acid solution in conduit 120 with hydrogen in conduit 130 in the presence of a catalyst in a reactor zone 125 to produce a decolorized carboxylic solution.

For the reactor zone 125, there are no special limitations in the form or construction thereof, subject to an arrangement that allows supply of hydrogen in conduit 130 to effect intimate contact of the crude carboxylic acid solution in conduit 120 with the catalyst in the reactor zone 125. Typically, the catalyst is usually a single Group VIII metal or combination of Group VIII metals. Preferably, the catalyst is selected from a group consisting of palladium, ruthenium, rhodium and combination thereof. Most preferably, the catalyst is palladium. Typically, the catalyst is supported, preferably on porous carbon.

The reactor zone 125 comprises a hydrogenation reactor that operates at a temperature and pressure sufficient to hydrogenate the characteristically yellow compounds in the crude carboxylic acid solution in conduit 120. By hydrogenation treatment, the characteristically yellow compounds in the crude carboxylic acid solution are converted to colorless derivatives. The b* color of in the decolorized carboxylic acid solution in conduit 135 is between about 0.5 to about 4. Preferably the b* color of the carboxylic acid solution in conduit 135 is between 0.5 to 2.0. Most preferably the b* color in the carboxylic solution in conduit 135 is between 0.5 to 1.5. The b* is one of the three-color attributes measured on a spectroscopic reflectance-based instrument. The color can be measure by any device known in the art. A Hunter Ultrascan XE instrument is typically the measuring device. Positive readings signify the degree of yellow (or absorbance of blue), while negative readings signify the degree of blue (or absorbance of yellow).

The hydrogen in conduit 130 is fed at a rate sufficient to convert the characteristically yellow compounds in the crude carboxylic slurry in conduit 120 to colorless derivatives; wherein the b* color is between about 0.5 to about 4.0 in the decolorized carboxylic acid solution in conduit 135

Step (3) comprises, optionally, flashing the decolorized carboxylic acid solution 135 in a flashing zone 145 to remove a portion of the water from the decolorized carboxylic acid solution in conduit 135. The flashing of the aqueous carboxylic solution 135 can be accomplished by any means know in the art. Typically, a vessel or a plurality of vessels are used to accomplish the flashing. In the flashing zone 145, water and residual hydrogen can be removed as a vapor via conduit 150. The flash vessel(s) operate at a temperature sufficient to remove a portion of the water. Alternatively, flashing zone 145 can be omitted as indicated by conduit 140.

Step (4) comprises, adding a diol in conduit 170 to the decolorized carboxytic acid solution in conduit 155. A portion of the water via conduit 165 is removed from an esterification reactor zone 160 to form said carboxylic acid/diol mixture in the esterification reactor zone 160. The carboxylic acid and diol subsequently reacts to form a hydroxy alkyl ester stream 175. The hydroxy alkyl ester stream 175 comprises a hydroxy alkyl ester compound.

The diol in conduit 170 is introduced in such a manner as to displace the water as the dominant slurrying liquid. This can be accomplished by introducing a diol via conduit 170 as a saturated liquid at a temperature which is sufficient to vaporize the water. Preferably, the diol in conduit 170 is introduced as a saturated or superheated vapor. The diol in conduit 170 is selected from the group consisting of ethylene glycol, diethylene glycol, n-butylene glycol, i-butylene glycol, n-propylene glycol, 1,4 butanediol, cyclohexanedimethanol, and mixtures thereof. Preferably, the diol in conduit 170 is ethylene glycol. Alternatively, an external heat source can be used to introduce sufficient enthalpy to vaporize the water, which exits via conduit 165. The hydroxalky ester stream exits via conduit stream 175.

The esterification reactor zone 160 operates at a temperature that is sufficient to produce a hydroxyethyl from the carboxylic acid mixture. The esterification reactor zone 160 comprises an esterification reactor. The esterification can be accomplished by any means know in the art.

In a third embodiment of this invention a process for producing a terephthalic acid/diol comprises vaporizing a decolorized terephthalic acid solution with a diol in an esterification reactor zone to remove a portion of the water to form the terephthalic acid/diol mixture; wherein the terephthalic acid and diol subsequently reacts in the esterification zone to form a hydroxy alkyl ester stream.

The esterification reactor zone, the decolorized terephthalic acid solution and a process to produce the decolorized terephthalic acid solution is described subsequently in a fourth embodiment of this invention.

In the forth embodiment of this invention a process for producing a terephthalic acid/diol mixture is provided as shown in FIG. #2.

Step (1) comprises mixing a crude terephthalic acid powder in conduit 205 with water in conduit 215 in a mixing zone 210 to form a crude terephthalic acid solution in conduit 220. The mixing of the crude terephthalic acid powder in conduit 205 with water in conduit 215 can be accomplished by any means known in the art. The starting feed material is the crude terephthalic acid powder in conduit 205 with some specific physical characteristics that differ from crude terephthalic acid described in U.S. Pat. No. 5,095,146 and U.S. Pat. No. 5,175,355, herein incorporated by reference. Specifically, the total amount of p-toluic acid and 4-carboxybenzaldehyde in the crude terephthalic acid powder in conduit 205 is less than about 900 ppm on a weight basis, preferably, less than about 500 ppm, and most preferably, less than about 250 ppm. Another characteristic of the crude terephthalic powder in conduit 205 is the color as measured by b* is less than about 7. Preferably, the color measured by b* is between 4 and 6.

The mixing zone 210 can be any vessel or equipment capable of mixing the crude terephthalic acid powder in conduit 205 with water in conduit 215. The crude terephthalic acid powder in conduit 205 is slurried in water in conduit 215 in the mixing zone 210 to produce the crude terephthalic acid solution in conduit 220. The crude terephthalic acid and water are heated in a mixing zone 210 to a temperature of about 230° C. or higher to dissolve the crude terephthalic acid powder in conduit 205 in the mixing zone 210 to produce the crude terephthalic acid solution in conduit 220. Preferably, the crude terephthalic slurry in the mixing zone 210 is heated to a temperature in the range of about 240° C. to about 300° C. The pressure of the mixing zone is about 900 psia to about 1400 psia to dissolve the crude terephthalic acid powder in conduit 205 in the mixing zone 210. Generally, the concentration of crude terephthalic acid in the crude terephthalic acid solution is about 15% to about 30% by weight, preferably, 20 to 30% by weight.

Step (2) is decolorizing the crude terephthalic acid solution in conduit 220 in a reactor zone 225 to form a decolorized terephthalic acid solution in conduit 235.

The decolorizing of the crude terephthalic acid solution in conduit 220 can be accomplished by any means known in the art. Preferably, the decolorizing can be accomplished by reacting the crude terephthalic acid solution in conduit 220 with hydrogen in conduit 230 in the presence of a catalyst in a reactor zone 225 to produce a decolorized terephthalic acid solution.

For the reactor zone 225, there are no special limitations in the form or construction thereof, subject to an arrangement that allows supply of hydrogen in conduit 230 to effect intimate contact of the crude terephthalic acid solution in conduit 220 with the catalyst in the reactor zone 225. Generally, the catalyst is usually a single Group VIII metal or combination of Group VIII metals. Preferably, the catalyst is selected from a group consisting of palladium, ruthenium, rhodium and combination thereof. Most preferably, the catalyst is palladium. Typically, the catalyst is supported, preferably on porous carbon.

The reactor zone 225 comprises a hydrogenation reactor which operates at a temperature of about 230° C. or higher. Preferably, the hydrogenation reactor operates in the range of about 240° C. to about 300° C. The hydrogenation reactor operates at a pressure of about 900 psia to about 1400 psia and at a hydrogen partial pressure of at least about 100 psia. Preferably, the hydrogen partial pressure is in the range of about 100 to about 300 psia. By hydrogenation treatment, the characteristically yellow compounds in the crude terephthalic acid solution are converted to colorless derivatives. In addition, the reactor zone converts a portion of 4-carboxybenzaldehyde to p-toluic acid. The hydrogen in conduit 230 is fed at a rate of at least about 1.5 times the molar ratio necessary to convert the 4-carboxybenzaldehyde in the crude terephthalic acid solution in conduit 220 to p-toluic acid. Preferably, the hydrogen 230 is fed at a rate of at least about 2.0 times the molar ratio necessary to convert the 4-carboxybenzaldehyde in the crude terephthalic acid solution 220 to p-toluic acid. The b* color is between about 0.5 to about 4 in the terephthalic acid decolorized solution in conduit 235. Preferably the b* color of the terephthalic acid solution in conduit 235 is between 0.5 to 2. Most preferably the b* color in the decolorized terephthalic acid solution in conduit 235 is between 0.5 to 1.5.

Step (3) comprises, optionally, flashing the decolorized terephthalic acid solution 235 in a flashing zone 245 to remove a portion of the water 250 from the aqueous terepthalic acid solution 235. The flashing of the aqueous terephthalic solution 235 can be accomplished by any means know in the art. Typically, a vessel or a plurality of vessels are used to accomplish the flashing. In the flashing zone 245, water and residual hydrogen can be removed as a vapor via conduit 250. The flash vessel(s) operate at a temperature of about 150° C. or higher. Preferably, the flash vessels(s) operate in the range of about 155° C. to about 260° C. The flash vessel(s) operate under a pressure of about 75 psia to about 1400 psia. Specific operating ranges vary depending on the amount of water removed via conduit 250. Alternatively, flashing zone 245 can be omitted as indicated by conduit 240.

Step (4) comprises, adding a diol in conduit 270 to the decolorized terephthalic acid solution in conduit 255 in an esterification reactor zone 260 to remove a portion of the water via conduit 265 to form said terephthalic acid/diol mixture in the esterification reactor zone 260. The carboxylic acid and diol react to form a hydroxyalkyester stream 275. The hydroxyalkyester stream 275 comprises a hydroxyalky ester compound.

The diol in conduit 270 is introduced in such a manner as to displace the water as the dominant slurrying liquid. This can be accomplished by introducing a diol via conduit 270 as a saturated liquid in a temperature range of 150° C. to 300° C. Preferably, the diol in conduit 270 is introduced as a saturated or superheated vapor in the temperature range of 150 to 300° C. in a form with sufficient enthalpy as to evaporate the water to exit via conduit 265. The diol in conduit 270 is selected from the group consisting of ethylene glycol, diethylene glycol, n-butylene glycol, i-butylene glycol, n-propylene glycol, 1,4 butanediol, cyclohexanedimethanol, and mixtures thereof. Preferably, the diol in conduit 270 is ethylene glycol. Alternatively, an external heat source can be used to introduce sufficient enthalpy to vaporize the water, which exits via conduit 265. The hydroxy alkyl ester stream mixture exits via conduit stream 275. Preferably, the diol in conduit 270 is ethylene glycol. Alternatively, an external heat source can be used to introduce sufficient enthalpy to vaporize the water, which exits via conduit 265. The hydroxalkyl ester stream mixture exits via conduit stream 275.

The esterification reactor zone 260 operates at a temperature of about 240° C. higher. Preferably the esterification reactor zone 260 operates in the temperature range of 260° C. to 280° C. The esterification reactor zone 260 operates under a pressure of about 40 psia to about 100 psia so as to effect esterification of the terephthalic acid/diol mixture 275 to produce a hydroxyethyl ester of terephthalic acid.

In a fifth embodiment of this invention, a process for producing a carboxylic acid/diol mixture comprises removing a portion of contaminated water in an aqueous slurry by adding a diol in a liquor removal zone to produce said carboxylic acid/diol mixture.

The liquor removal zone, the aqueous slurry and a process to produce the aqueous slurry are described subsequently in a sixth embodiment of this invention.

In the six embodiment of this invention, a process for producing a carboxylic acid/diol mixture is provided as shown in FIG. #3.

Step (1) comprises mixing a crude carboxylic acid powder in conduit 305 with water in conduit 315 in a mixing zone 310 to form a crude carboxylic acid solution in conduit 320. The mixing of the crude carboxylic powder in conduit 305 with water in conduit 315 in the mixing zone 310 can be accomplished by any means known in the art. The starting feed material is the crude carboxylic acid powder in conduit 305. Typically, the carboxylic acid is selected from a group consisting of terephthalic acid, isophthalic acid, naphthalene dicarboxylic acid, and mixtures thereof. The mixing zone 310 can be any vessel or equipment capable of mixing the crude carboxylic acid powder in conduit 305 with water in conduit 315.

The crude carboxylic acid powder in conduit 305 and water in conduit 315 in mixing zone 310 is heated to a temperature sufficient to dissolve the crude carboxylic acid powder in conduit 305 in the mixing zone 310 to produce the crude carboxylic acid solution in conduit 320. The pressure of the mixing zone 310 is a pressure sufficient to dissolve the crude carboxylic acid powder in conduit 305 in the mixing zone 310. Generally, the concentration of crude carboxylic acid in the crude carboxylic acid solution is about 15% to about 35% by weight.

Step (2) is decolorizing the crude carboxylic acid solution in conduit 320 in a reactor zone 325 to form an decolorized carboxylic acid solution in conduit 330.

The decolorizing of the crude carboxylic acid solution in conduit 320 can be accomplished by any means known in the art. Preferably, the decolorizing can be accomplished by reacting the crude carboxylic acid solution in conduit 320 with hydrogen in conduit 330 in the presence of a catalyst in a reactor zone 325 to produce a decolorized carboxylic acid solution.

For the reactor zone 325, there are no special limitations in the form or construction thereof, subject to an arrangement that allows supply of hydrogen in conduit 330 to effect intimate contact of the crude carboxylic slurry 320 with the catalyst in the reactor zone. Typically, the catalyst is usually a single Group VIII metal or combination of Group VIII metals. Preferably, the catalyst is selected from a group consisting of palladium, ruthenium, rhodium and combinations thereof. Most preferably, the catalyst is palladium. Typically, the catalyst is supported, preferably on porous carbon.

The reactor zone 325 comprises a hydrogenation reactor that operates at a temperature sufficient to convert the characteristically yellow compounds in the crude carboxylic acid solution 320 to colorless derivatives. The b* color of in the decolorized carboxylic acid solution in conduit 335 is between about 0.5 to about 4. Preferably the b* color of the carboxylic acid solution in conduit 335 is between 0.5 to 2. Most preferably the b* color in the decolorized carboxylic acid solution in conduit 335 is between 0.5 to 1.5.

The hydrogen in conduit 330 is fed at a rate sufficient to convert the characteristically yellow compounds in the crude carboxylic slurry in conduit 320 to colorless derivatives; wherein the b* color is between about 0.5 to about 4 in the decolorized carboxylic acid solution in conduit 335.

Step (3) comprises crystallizing the decolorized carboxylic acid solution in conduit 335 in a crystallization zone 345 to form an aqueous slurry in conduit 355.

The crystallization zone 345 comprises a vessel or plurality of vessels capable of removing water from the decolorized carboxylic acid solution in conduit 335 to produce an aqueous slurry in conduit 355. Typically, the vessels comprise at least one crystallizer. Examples of such systems can be found in U.S. Pat. Nos. 5,567,842 and 3,931,305, herein incorporated by reference. Generally, the aqueous slurry in conduit 355 has a carboxylic acid concentration of from 10 to 60 weight percent. The temperature range of the carboxylic acid solution in the crystallization zone 345 is that which is sufficient to remove a portion of the water.

Step (4) comprises removing a portion of contaminated water via conduit 365 in the aqueous slurry 355 by adding a diol in conduit 370 in a liquor removal zone 360 to produce the carboxylic acid/diol mixture in conduit 375.

The purpose of the liquor removal zone 360 is to replace the contaminated-water with a diol in conduit 370. The contaminated water comprises water and typical contaminants. The diol in conduit 370 is selected from the group consisting of ethylene glycol, diethylene glycol, n-butylene glycol, i-butylene glycol, n-propylene glycol, 1,4 butanediol, cyclohexanedimethanol, and mixtures thereof. Preferably, the diol in conduit 370 is ethylene glycol. The diol in conduit 370 is introduced into the liquor removal zone 360 via conduit 370. The removal of the contaminated water via conduit 365 in the liquor removal zone 360 can be accomplished using variety of techniques including, but not limited to, cyclones, centrifuges, and filters. The key factor in the liquor removal zone 360 is to select a temperature range where the typical contaminants preferably remain with the aqueous mother liquor instead of remaining with the carboxylic acid. The resultant carboxylic acid/diol mixture is removed via conduit 375. The resultant carboxylic acid/diol mixture in conduit 375 is adequate as feed material for the esterification of carboxylic acid with the diol to produce the ester of carboxylic acid.

In a seventh embodiment of this invention, a process for producing a terephthalic acid/diol mixture comprises removing a portion of the p-toluic contaminated water in a terephthalic acid aqueous aqueous slurry by adding a diol in a liquor removal zone to produce said terephthalic acid/diol mixture.

The liquor removal zone, the terephthalic acid aqueous slurry and a process to produce the aqueous slurry are described subsequently in an eight embodiment of this invention.

In the eight embodiment of this invention, a process for producing a terephthalic acid/diol mixture is provided as shown in FIG. #4.

Step (1) comprises mixing a crude terephthalic acid powder in conduit 405 with water in conduit 415 in a mixing zone 410 to form a crude terephthalic acid solution in conduit 420. The mixing of the crude terephthalic powder in conduit 405 with water in conduit 415 in the mixing zone 410 can be accomplished by any means known in the art. The starting feed material is the crude terephthalic acid powder in conduit 405. The total amount of p-toluic acid and 4-carboxybenzaldehyde in the crude terephthalic acid powder in conduit 405 is less than about 6000 ppm on a weight basis. Another characteristic of the crude terephthalic powder 405 is the color as measured by b* is less than about 7. Preferably the color measured by b* is between 4 and 6. This crude terephthalic acid powder in conduit 405 is introduced into a mixing zone 410. The mixing zone 410 can be any vessel or equipment capable of mixing the crude terephthalic acid powder in conduit 405 with water in conduit 415.

The crude terephthalic acid powder and water are heated to a temperature of about 230° C. or higher to dissolve the crude terephthalic acid powder in conduit 405 in the mixing zone 410 to produce the crude terephthalic acid solution in conduit 420. Preferably, the crude terephthalic acid solution in the mixing zone 410 is heated to a temperature in the range of about 240° C. to about 300° C. The pressure of the mixing zone 410 is about 900 psia to about 1400 psia to dissolve the crude terephthalic acid powder in conduit 405 in the mixing zone 410. Generally, the concentration of crude terephthalic acid powder 405 in the crude terephthalic acid solution 420 is in a range of about 15% to about 35% by weight, preferably 20 to 30% by weight.

Step (2) is decolorizing the crude terephthalic acid solution in conduit 420 in a reactor zone 425 to form a decolorized terephthalic acid solution in conduit 435.

The decolorizing of the crude carboxylic acid solution in conduit 420 can be accomplished by any means known in the art. Preferably, the decolorizing can be accomplished by reacting the crude carboxylic acid solution in conduit 420 with hydrogen in conduit 430 in the presence of a catalyst in a reactor zone 425 to produce a decolorized carboxylic acid solution.

For the reactor zone 425, there are no special limitations in the form or construction thereof, subject to an arrangement that allows supply of hydrogen in conduit 430 to effect contact of the crude terephthalic slurry 420 with the catalyst in the reactor zone. The catalyst is usually a single Group VIII metal or combination of Group VIII metals. Preferably, the catalyst is selected from a group consisting of palladium, ruthenium, rhodium and combinations thereof. Most preferably, the catalyst is palladium. Typically, the catalyst is supported, preferably on porous carbon.

The reactor zone 425 comprises a hydrogenation reactor which operates at a temperature of about 230° C. or higher. Preferably the hydrogenation reactor operates in the range of about 240° C. to about 300° C. The hydrogenation reactor operates at a pressure of about 900 psia to about 1400 psia and at a hydrogen partial pressure of at least about 100 psia. Preferably, the hydrogen partial pressure is in the range of about 100 to about 300 psia. By hydrogenation treatment, the characteristically yellow compounds in the crude terephthalic acid solution 420 are converted to colorless derivatives. In addition, the reactor zone converts a portion of 4-carboxybenzaldehyde to p-toluic acid.

The hydrogen in conduit 430 is fed at a rate of at least about 1.5 times the molar ratio necessary to convert the 4-carboxybenzaldehyde in the crude terephthalic slurry 420 to p-toluic acid. Preferably the hydrogen 430 is fed at a rate of at least about 2.0 times the molar ratio necessary to convert the 4-carboxybenzaldehyde in the crude terephthalic slurry 420 to p-toluic acid. The b* color is between about 0.5 to about 4 in the decolorized terephthalic acid solution in conduit 435. Preferably the b* color of the terephthalic acid solution in conduit 435 is between 0.5 to 2. Most preferably the b* color in the decolorized terephthalic acid solution in conduit 435 is between 0.5 to 1.5.

Step (3) comprises crystallizing said decolorized terephthalic acid solution in conduit 435 in a crystallization zone 445 to form a terephthalic acid aqueous slurry in conduit 455.

The crystallization zone 445 comprises a vessel or plurality of vessels capable of removing water via conduit 450 from the decolorized terephthalic acid solution in conduit 435 to produce an terephthalic acid aqueous slurry in conduit 455. Typically the vessels comprise at least one crystallizer as previously described. Generally, the terephthalic acid aqueous slurry in conduit 455 has a terephthalic acid concentration of from 10 to 60 weight percent, preferably from 20 to 40 weight percent. Examples of such systems can be found in U.S. Pat. Nos. 5,567,842 and 3,931,305 both of which are herein incorporated by reference. The temperature range of the terephthalic acid aqueous slurry in conduit 455 is from about 120° C. to about 270° C. The pressure range of the crystallizing is from about 75 to about 1400 psia.

Step (4) comprises removing a portion of p-toluic acid contaminated water via conduit 465 in the terephthalic acid aqueous slurry 455 by adding a diol in conduit 470 in a liquor removal zone 460 to produce said terephthalic acid/diol mixture in conduit 475.

The purpose of the liquor removal zone 460 is to replace the p-toluic acid contaminated water with a diol in conduit 470. The diol in conduit 470 is selected from a group consisting of ethylene glycol, diethylene glycol, n-butylene glycol, i-butylene glycol, n-propylene glycol, 1,4 butanediol, cyclohexanedimethanol, and mixtures thereof. Preferably, the diol in conduit 470 is ethylene glycol. The diol in conduit 470 is introduced into the liquor removal zone 460 via conduit 470. The removal of the p-toluic acid contaminated water via conduit 465 in the liquor removal zone 460 can be accomplished using variety of techniques including, but not limited to, cyclones, centrifugation, and filtration. The key factor in the liquor removal zone 460 is to select a temperature range where the p-toluic acid and 4-carboxybenzaldehyde will preferably remain with the aqueous mother liquor instead of remaining with the terephthalic acid. The liquor removal zone 460 operates in a range of about 120° C. to about 270° C., preferably in the range of 120° C. to 150° C. The p-toluic acid contaminated water is removed via conduit 465. The resultant terephthalic acid/diol mixture is removed via conduit 475. The resultant terephthalic acid/diol mixture in conduit 475 is adequate as feed material for the esterification of terephthalic acid with a diol to produce the ester of terephthalic acid.

I claim:

1. A process for producing a carboxylic acid/diol mixture, said process comprising adding a decolorized carboxylic acid composition comprising a carboxylic acid and water in an esterification reactor zone and adding a diol to said decolorized carboxylic acid composition in said esterification zone; wherein said diol is added to remove a portion of said water by vaporization from said decolorized carboxylic acid composition to form said carboxylic acid/diol mixture comprising a hydroxy alkyl ester.

2. A process according to claim 1 wherein said carboxylic acid is selected from a group consisting of terephthalic acid, isophthalic acid, naphthalene dicarboxylic acid, and mixtures thereof.

3. A process for producing a carboxylic acid/diol mixture, said process comprising:
(a) mixing a crude carboxylic acid powder with water in a mixing zone to form a crude carboxylic acid solution; wherein said carboxylic acid is selected from a group consisting of terephthalic acid, isophthalic acid, naphthalene dicarboxylic acid, and mixtures thereof;
(b) decolorizing said crude carboxylic acid composition in a reactor zone to produce a decolorized carboxylic acid composition;
(c) optionally, flashing said decolorized carboxylic acid composition in a flashing zone to remove a portion of the water from said decolorized carboxylic acid composition; and
(d) adding said decolorized carboxylic acid composition comprising a carboxylic acid and water in an esterification reactor zone and adding a diol to said decolorized carboxylic acid composition in said esterification zone; wherein said diol is added to remove a portion of the water by vaporization from said decolorized carboxylic acid composition to form said carboxylic acid/diol mixture comprising a hydroxy alkyl ester.

4. A process according to claim 3 wherein said decolorizing is accomplished by reacting said crude carboxylic acid composition with hydrogen in the presence of a catalyst in a reactor zone to produce said decolorized carboxylic acid composition; wherein said catalyst comprises a group VIII metal or combination thereof.

5. A process according to claim 1 or 3 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

6. A process according to claim 4 wherein said catalyst in said reactor zone comprises a group VIII metal or combination thereof.

7. A process according to claim 1 wherein said carboxylic acid is terephthalic acid.

8. A process for producing a terephthalic acid/diol mixture, said process comprising:
(a) mixing a crude terephthalic acid powder with water in a mixing zone to form a crude terephthalic acid composition;
(b) decolorizing said crude terephthalic acid composition in a reactor zone to form a decolorized terephthalic acid composition;
(c) optionally, flashing said decolorized terephthalic acid composition in a flashing zone to remove a portion of the water from said decolorized terephthalic acid composition; and
(d) adding said decolorized terephthalic acid composition comprising terephthalic acid and water in an esterification reactor zone and adding a diol to said decolorized carboxylic acid composition in said esterification zone; wherein said diol is added to remove a portion of the water by vaporization to form said terephthalic acid/diol mixture comprising a hydroxy alkyl ester.

9. A process according to claim 8 wherein said decolorizing is accomplished by reacting said crude terephthalic acid composition with hydrogen in the presence of a catalyst in said reactor zone to produce a said decolorized terephthalic acid composition; wherein said catalyst comprises a group VIII metal or combination thereof.

10. A process according to claim 8 wherein said crude terephthalic acid powder contains a concentration of p-toluic acid and 4-carboxybenzaldehyde less than about 900 ppm by weight.

11. A process according to claim 8 wherein said diol is selected from the group consisting of ethylene glycol, diethylene glycol, n-butylene glycol, i-butylene glycol, n-propylene glycol, 1,4 butanediol, cyclohexanedimethanol, and mixtures thereof.

12. A process according to claim 8 wherein said diol is ethylene glycol.

13. A process according to claim 8 wherein said crude terephthalic powder has a b* color less than about 7.

14. A process according to claim 8 wherein said mixing occurs at a pressure between about 900 psia to about 1400 psia.

15. A process according to claim 8 wherein the concentration of crude terephthalic acid in said crude terephthalic acid composition is in a range between about 15% to about 35% by weight.

16. A process according to claim 9 wherein said reacting occurs at a temperature greater than about 230° C.

17. A process according to claim 9 wherein said reacting occurs at a pressure between about 900 psia to about 1400 psia.

18. A process according to claim 9 wherein said reacting occurs at a hydrogen flow rate of about 1.5 times the molar ratio necessary to convert 4-carboxybenzaldehyde to p-toluic acid in said crude terephthalic acid composition.

19. A process according to claim 9 wherein said catalyst in said reactor zone comprises a group VIII metal or combination thereof.

20. A process according to claim 8 wherein said flashing occurs at a temperature greater than about 150° C.

21. A process according to claim 8 wherein said flashing occurs at a pressure between about 75 psia to about 1400 psia.

22. A process according to claim 8 wherein said adding occurs at a temperature greater than about 240° C.

23. A process according to claim 8 wherein said diol is introduced into said esterification reactor zone at a temperature between about 150° C. to about 300° C.

24. A process according to claim 8 wherein said adding occurs at a pressure between about 40 psia to about 100 psia.

25. A process for producing a terephthalic acid/ethylene glycol mixture, said process comprising:

(a) mixing a crude terephthalic acid powder with water in a mixing zone to form a crude terephthalic acid composition wherein said mixing zone is operated at a temperature greater than about 230° C., wherein the pressure in said mixing zone is in a range of about 900 psia to about 1400 psia; wherein the concentration of said crude terephthalic acid in said crude terephthalic acid composition is in a range of about 15% to about 35% by weight; wherein the color of said crude terephthalic acid powder is less than about 7 measured by b*; wherein the total concentration of p-toluic and 4-carboxybenzaldehyde in said crude terephthalic acid powder is less than about 900 ppm by weight;

(b) decolorizing said crude terephthalic acid composition with hydrogen in a reactor zone in the presence of a catalyst to form a decolorized terephthalic acid composition; wherein said catalyst comprises a group VIII metal or combination thereof; wherein said hydrogen is introduced into said reactor zone at a flow rate of about 1.5 times the molar ratio necessary to convert 4-carboxybenzaldehyde to p-toluic acid in said crude terephthalic acid composition; wherein said reacting occurs at a temperature greater than about 230° C., wherein said reacting occurs at a pressure between about 900 psia to about 1400 psia;

(c) optionally, flashing said decolorized terephthalic acid composition in a flashing zone to remove a portion of water from said decolorized terephthalic acid composition wherein said flashing zone comprises at least one flash vessel operated at a pressure in the range of about 75 psia to about 1400 psia; and wherein said vessel is operated at a temperature in a range greater than about 150° C.; and (d) adding said decolorized terephthalic acid composition in an esterification reactor zone and adding a diol to said decolorized carboxylic acid composition in said esterification zone to remove a portion of water by vaporization to form said terephthalic acid/ethylene glycol mixture comprising a hydroxy alkyl ester; wherein said diol is ethylene glycol at a temperature in a range of about 150° C. to about 300° C.

\* \* \* \* \*